(12) United States Patent
Wyzgala et al.

(10) Patent No.: US 6,416,526 B1
(45) Date of Patent: Jul. 9, 2002

(54) EXPANDABLE ATHERECTOMY BURR

(75) Inventors: Mark Wyzgala, Bellevue; Donald Baumgarten, Seattle; Lucas S. Gordon, Redmond; Eric B. Hamilton, Bothell; Matt Hefner, Puyallup; Tom Hiblar, Everett; Edward Wulfman, Woodinville, all of WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/589,861

(22) Filed: Jun. 8, 2000

Related U.S. Application Data

(63) Continuation of application No. 09/178,449, filed on Oct. 23, 1998, now Pat. No. 6,096,054.
(60) Provisional application No. 60/076,963, filed on Mar. 5, 1998.

(51) Int. Cl.$^7$ ............................................... A61B 17/32
(52) U.S. Cl. ....................................... 606/170; 606/180
(58) Field of Search ................................ 606/159, 170, 606/180

(56) References Cited

U.S. PATENT DOCUMENTS

| 2,701,559 A | 2/1955 | Cooper |
| 3,614,953 A | 10/1971 | Moss |
| 3,896,815 A | 7/1975 | Fettel et al. |
| 4,273,128 A | 6/1981 | Lary |
| 4,465,072 A | 8/1984 | Taheri |
| 4,589,412 A | 5/1986 | Kensey |
| 4,631,052 A | 12/1986 | Kensey |
| 4,653,496 A | 3/1987 | Bundy et al. |
| 4,685,458 A | 8/1987 | Leckrone |
| 4,696,667 A | 9/1987 | Masch |
| 4,728,319 A | 3/1988 | Masch |
| 4,747,821 A | 5/1988 | Kensey et al. |

(List continued on next page.)

FOREIGN PATENT DOCUMENTS

| DE | 867 144 | 2/1953 |
| EP | 0 086 048 | 8/1983 |
| EP | 0 204 218 A1 | 12/1986 |

OTHER PUBLICATIONS

PCT International Search Report, Int'l Publication No. WO 99/44513, International Publication Date: Sep. 10, 1999.

Primary Examiner—Jeffrey A. Smith
(74) Attorney, Agent, or Firm—Christensen O'Connor Johnson Kindness PLLC

(57) ABSTRACT

An atherectomy burr has an operating diameter that is larger than the diameter of a catheter in which the burr is routed. The burr may include a polymeric balloon that is coated with an abrasive and that expands when the burr is rotated. Alternatively, the burr may include a polymeric tube that is coated with an abrasive and secured to the proximal end of the burr. When the burr is rotated, the polymeric tube expands by centrifugal force. Alternatively, the burr may comprise a metallic strip wound over a mandrel. When the strip is tightly coiled to the mandrel, its outer diameter decreases. The outer diameter of the burr increases as the metallic strip expands. In addition, the burr can be formed as a wire spring wound over a drive tube. The distal end of the spring is coupled to a nose cone that can move within a distal lumen in the drive tube. The maximum expansion of the burr is controlled by the distance that the nose cone can be retracted into the lumen. In addition, the present invention includes a burr having an indexable outer diameter. Various indexing mechanisms are disclosed for selectively increasing or decreasing the distance between a proximal and distal end of the burr. As the length of the burr changes, the outer diameter of a number of cutting blades is changed to allow a physician to create different sized lumens in a patient's vessel.

1 Claim, 9 Drawing Sheets

U.S. PATENT DOCUMENTS

| | | | |
|---|---|---|---|
| 4,765,332 | A | 8/1988 | Fischell et al. |
| 4,781,186 | A | 11/1988 | Simpson et al. |
| 4,784,636 | A | 11/1988 | Rydell |
| 4,794,928 | A | 1/1989 | Kletschka |
| 4,794,931 | A | 1/1989 | Yock |
| 4,857,045 | A | 8/1989 | Rydell |
| 4,886,061 | A | 12/1989 | Fischell et al. |
| 4,898,574 | A | 2/1990 | Uchiyama et al. |
| 4,921,484 | A | 5/1990 | Hillstead |
| 4,926,858 | A | 5/1990 | Gifford, III et al. |
| 4,950,238 | A | 8/1990 | Sullivan |
| 4,966,604 | A | 10/1990 | Reiss |
| RE33,569 | E | 4/1991 | Gifford, III et al. |
| 5,030,201 | A | 7/1991 | Palestrant |
| 5,100,425 | A | 3/1992 | Fischell et al. |
| 5,154,724 | A | 10/1992 | Andrews |
| 5,158,564 | A | 10/1992 | Schnepp-Pesch et al. |
| 5,176,693 | A | 1/1993 | Pannek, Jr. |
| 5,192,291 | A | 3/1993 | Pannek, Jr. |
| 5,217,474 | A | 6/1993 | Zacca et al. |
| 5,224,945 | A | 7/1993 | Panneck, Jr. |
| 5,250,060 | A | 10/1993 | Carbo et al. |
| 5,308,354 | A | 5/1994 | Zacca et al. |
| 5,312,427 | A | 5/1994 | Shturman |
| 5,314,438 | A | 5/1994 | Shturman |
| 5,318,576 | A | 6/1994 | Plassche, Jr. et al. |
| 5,336,234 | A | 8/1994 | Vigil et al. ............... 606/159 |
| 5,356,418 | A | 10/1994 | Shturman |
| 5,360,432 | A | 11/1994 | Shturman |
| 5,376,100 | A | 12/1994 | Lefebvre |
| 5,395,311 | A | 3/1995 | Andrews |
| 5,402,790 | A | 4/1995 | Jang et al. |
| B14,842,579 | | 10/1995 | Shiber |
| 5,490,859 | A | 2/1996 | Mische et al. |
| 5,554,163 | A | 9/1996 | Shturman |
| 5,556,405 | A | 9/1996 | Lary |
| 5,556,408 | A | 9/1996 | Farhat |
| 5,569,276 | A | 10/1996 | Jang et al. |
| 5,571,086 | A | 11/1996 | Kaplan et al. |
| 5,571,122 | A | 11/1996 | Kelly et al. |
| B14,990,134 | | 11/1996 | Auth |
| 5,616,149 | A | 4/1997 | Barath |
| 5,649,941 | A | 7/1997 | Lary |
| 5,653,696 | A | 8/1997 | Shiber |
| 5,681,336 | A | 10/1997 | Clement et al. |
| 5,697,944 | A | 12/1997 | Lary |
| 5,725,543 | A | 3/1998 | Redha |
| 5,725,568 | A | 3/1998 | Hastings |
| 5,728,123 | A | 3/1998 | Lemelson et al. |
| 5,749,914 | A | 5/1998 | Janssen |
| 5,766,192 | A | 6/1998 | Zacca |
| 5,792,158 | A | 8/1998 | Lary |
| 5,836,957 | A | 11/1998 | Schulz et al. |
| 5,842,479 | A | 12/1998 | Plaia et al. |
| 5,868,708 | A | 2/1999 | Hart et al. ............... 604/104 |
| 5,897,566 | A | 4/1999 | Shturman et al. |
| 5,897,567 | A | 4/1999 | Ressemann et al. |
| 5,902,263 | A | 5/1999 | Patterson |
| 5,919,200 | A | 7/1999 | Stambaugh et al. ........ 606/159 |
| 6,096,054 | A * | 8/2000 | Wyzgala et al. ............ 606/170 |

* cited by examiner

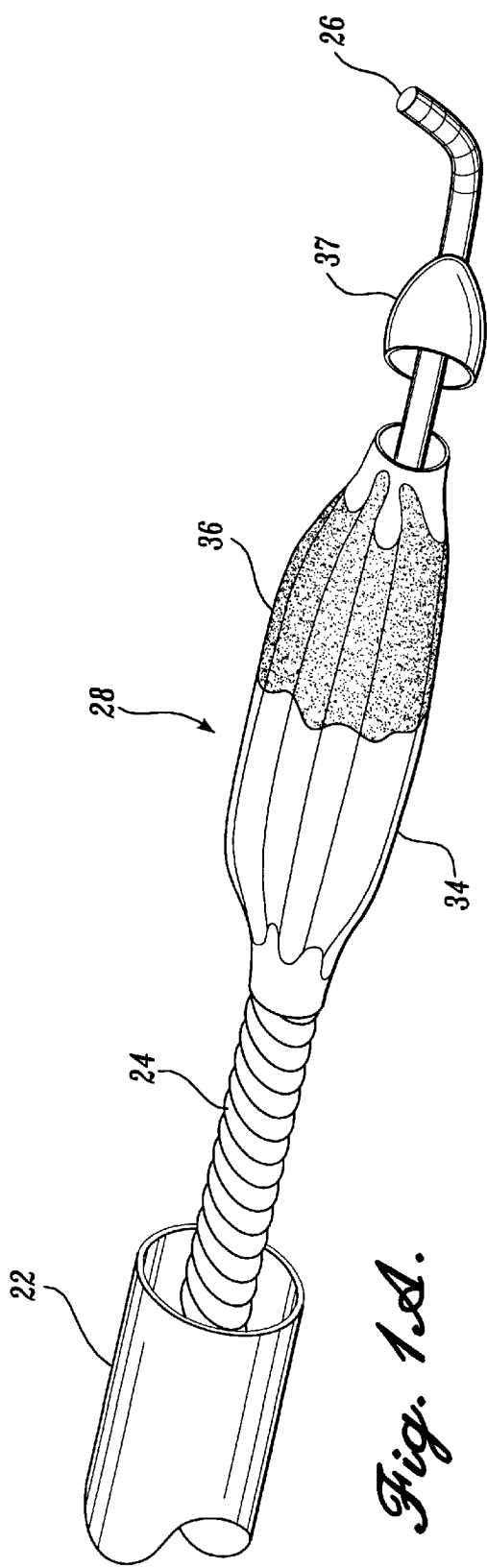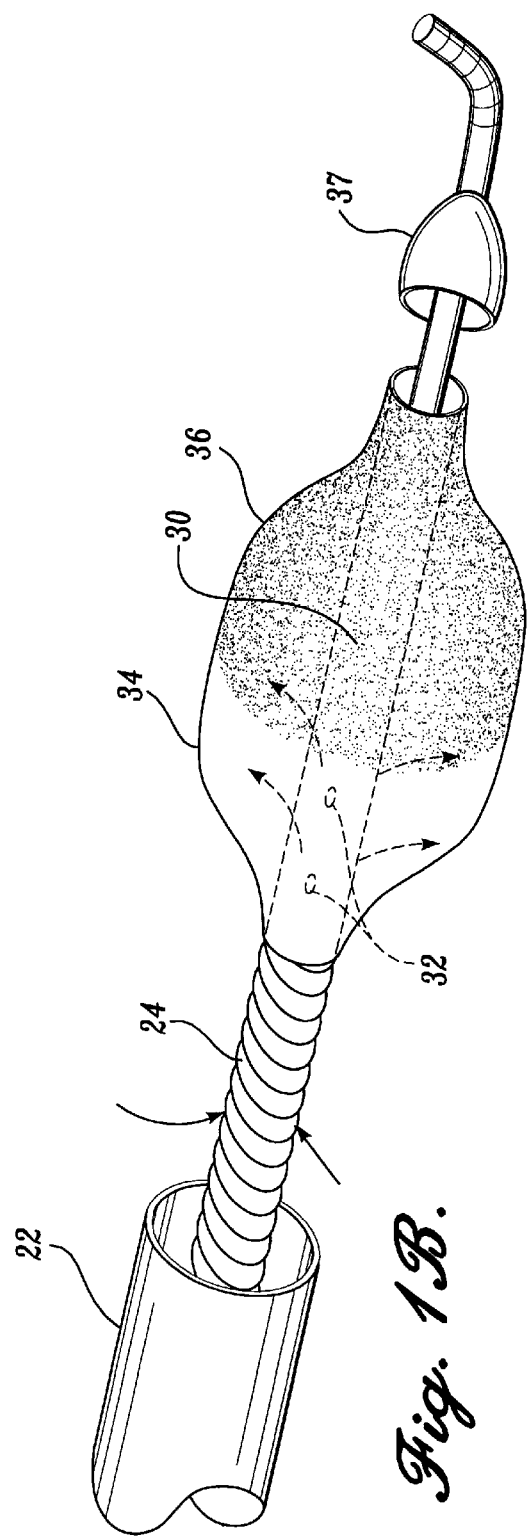

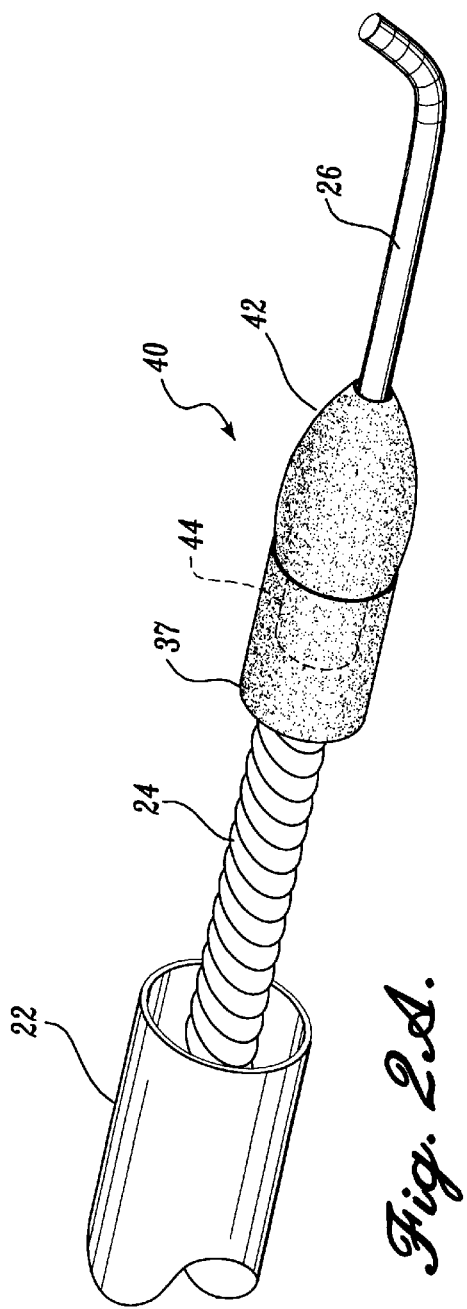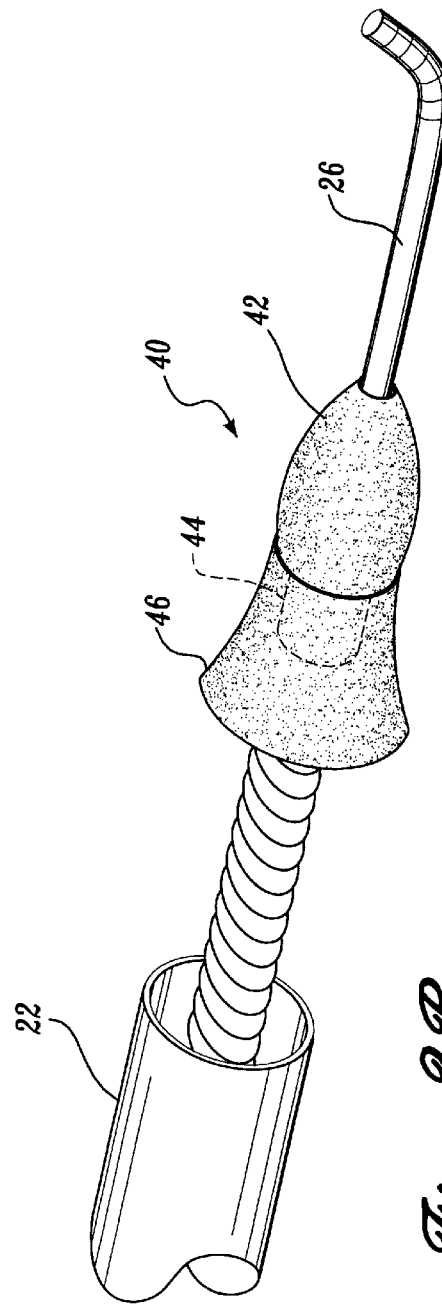

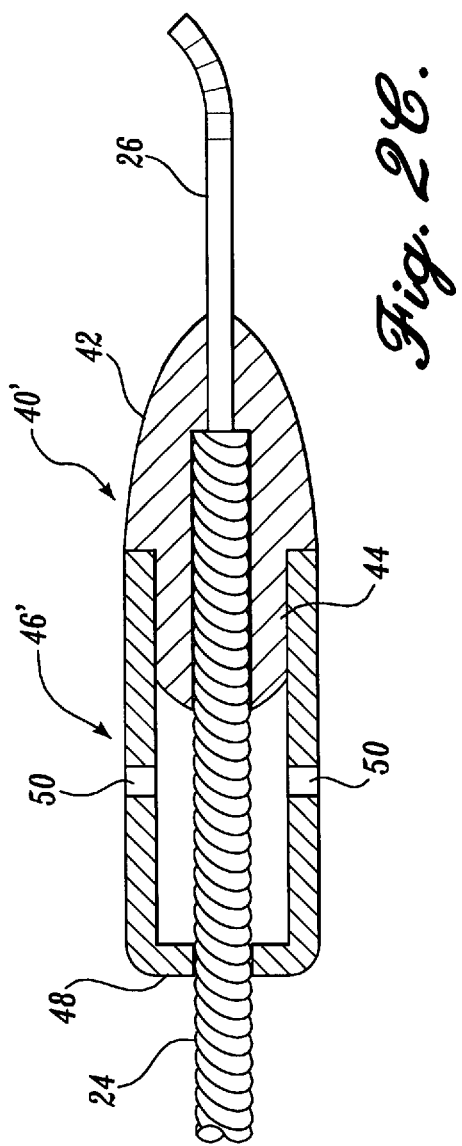
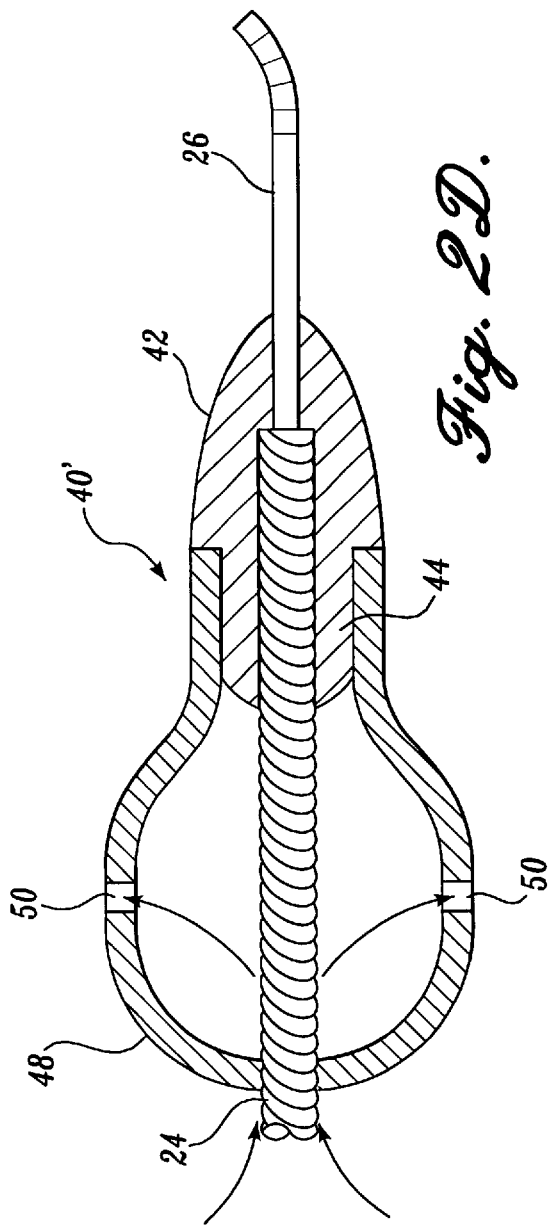

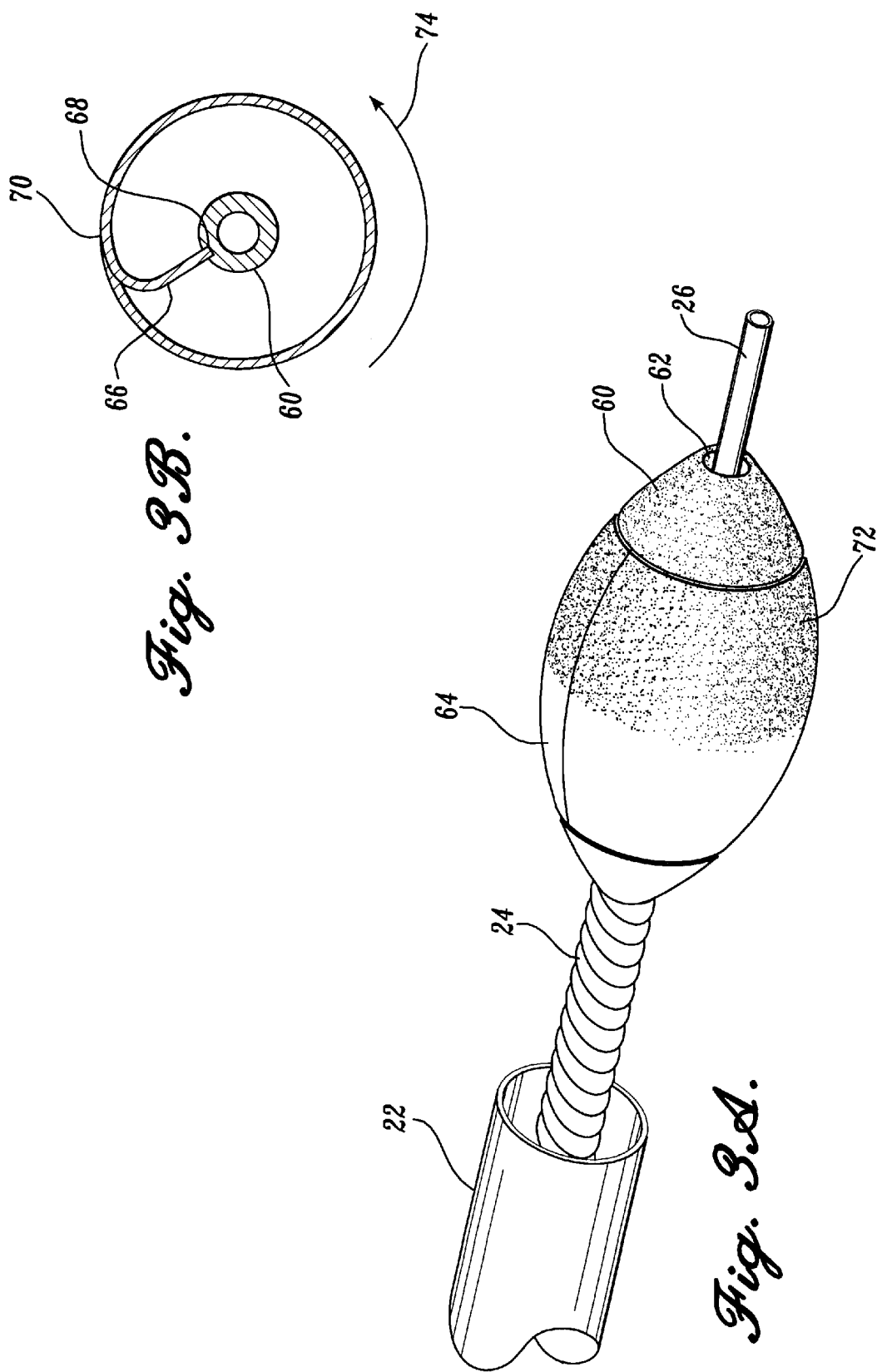

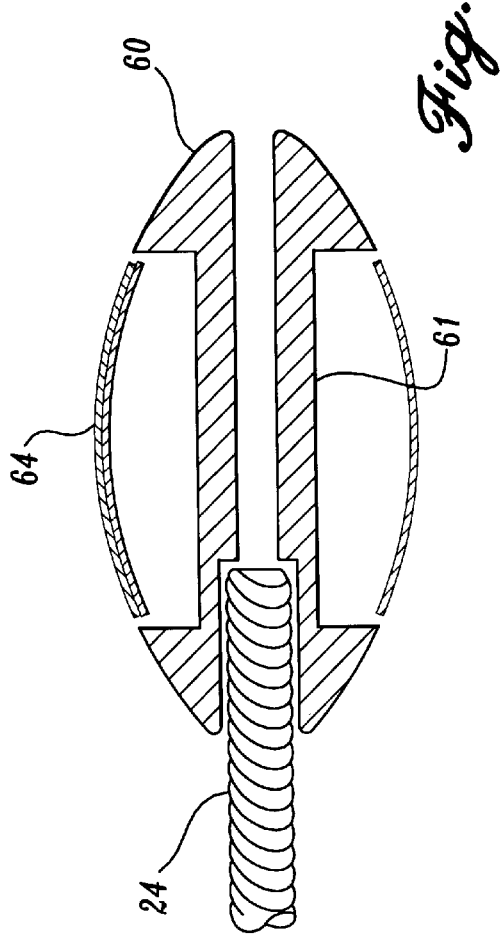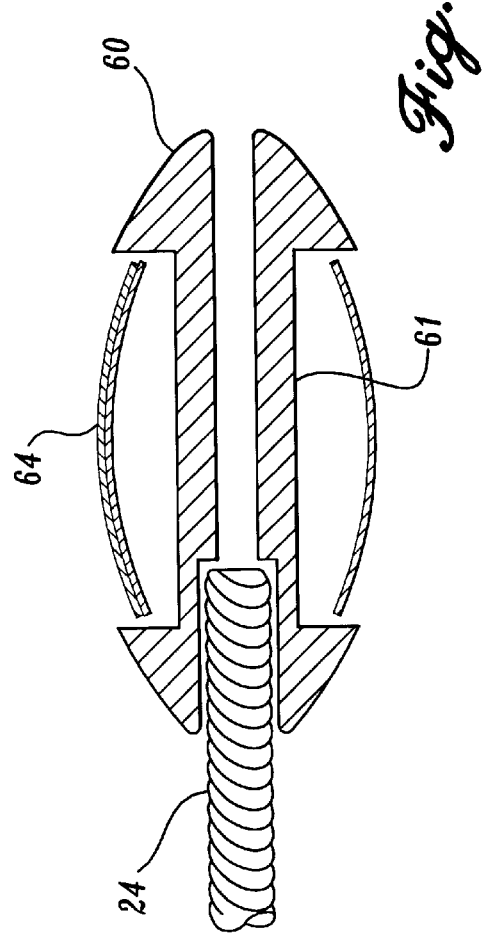

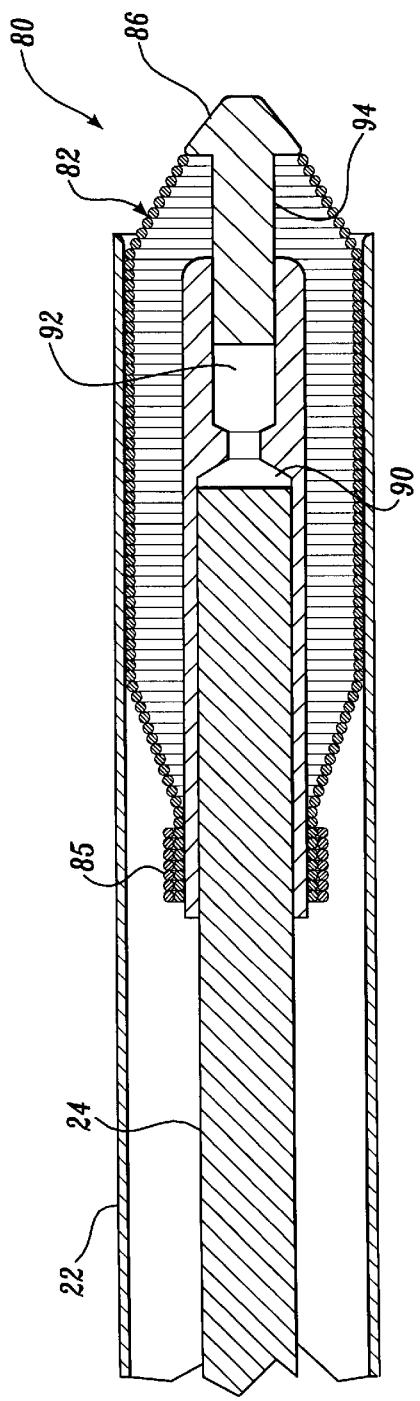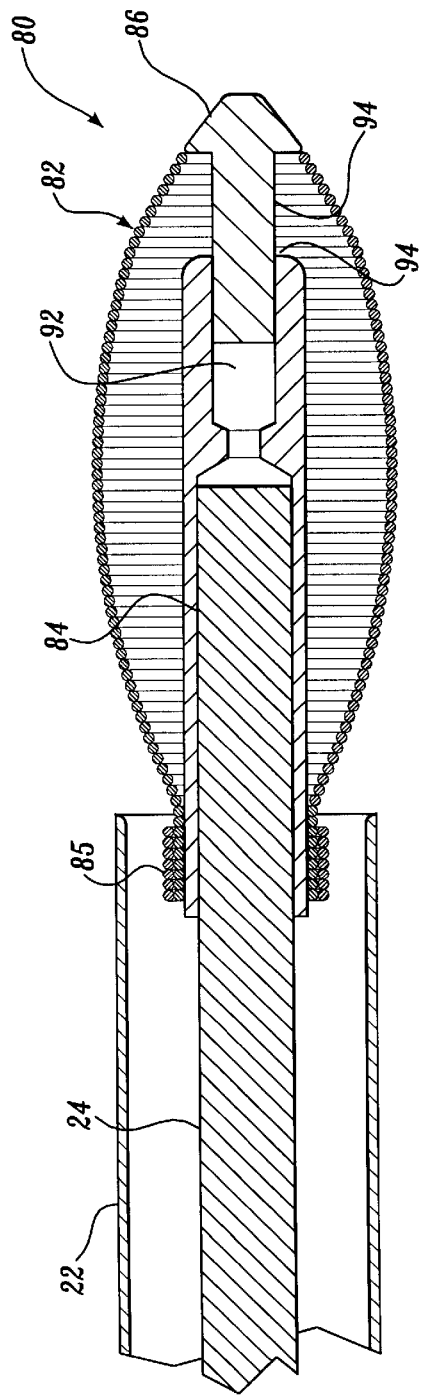

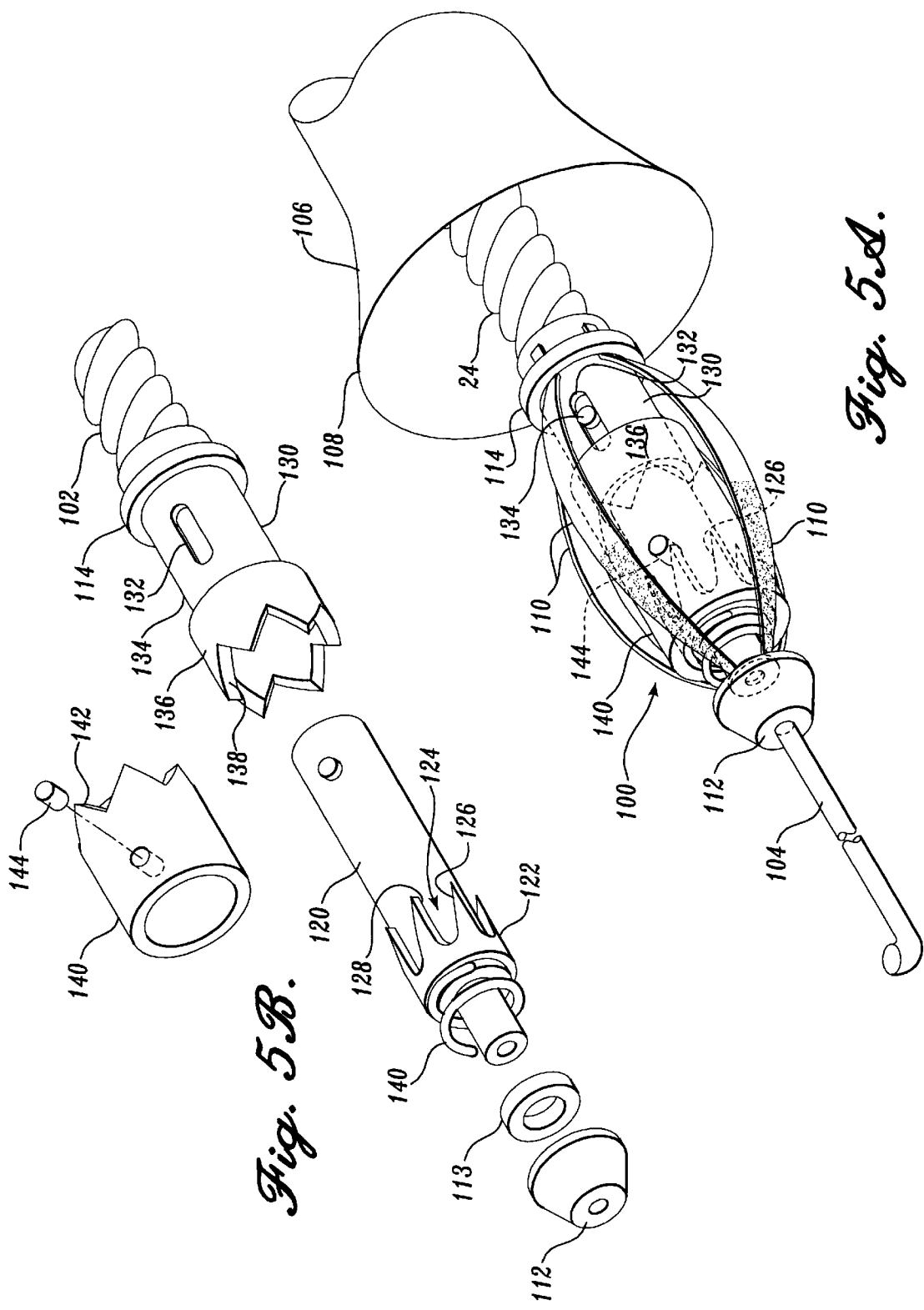

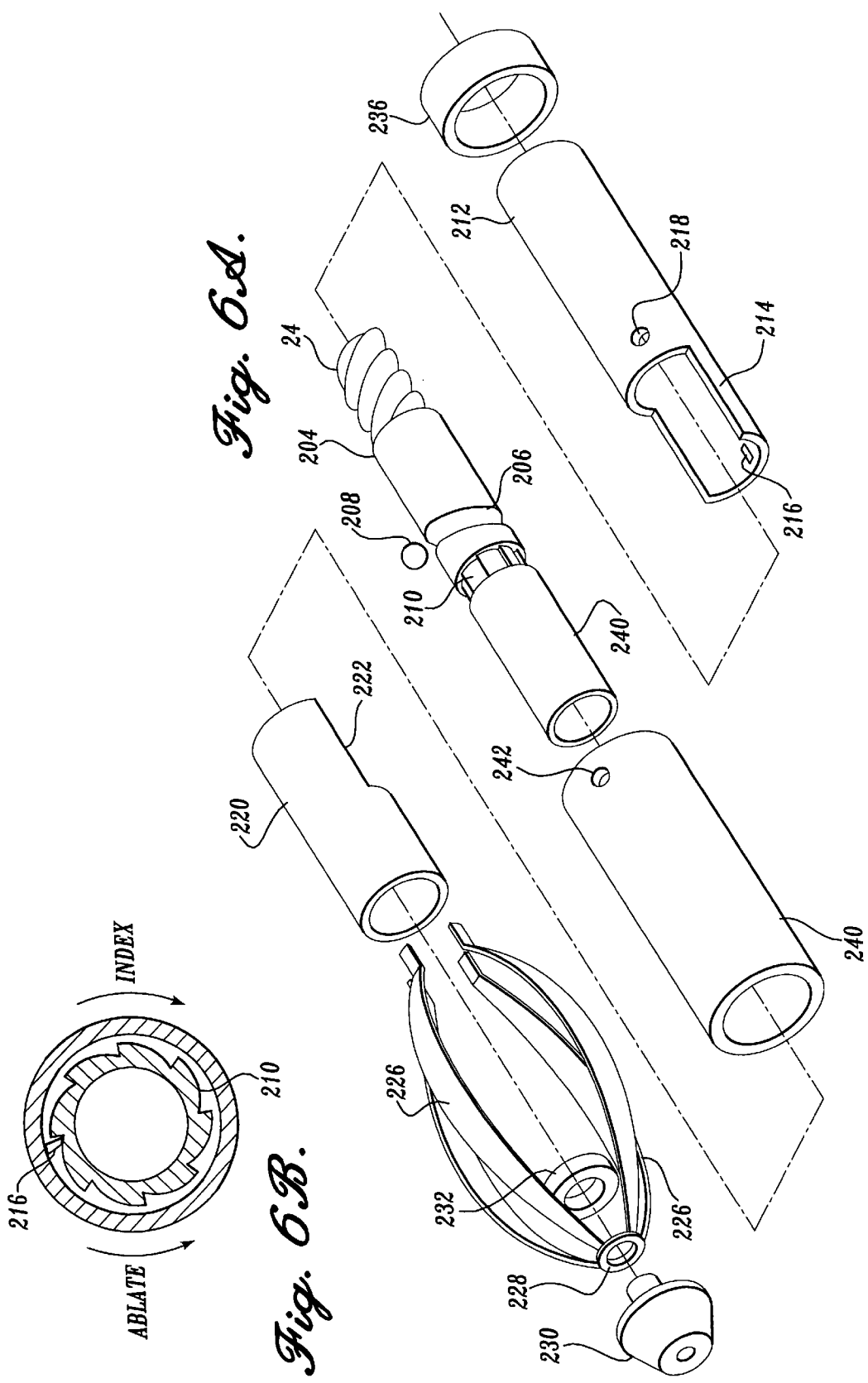

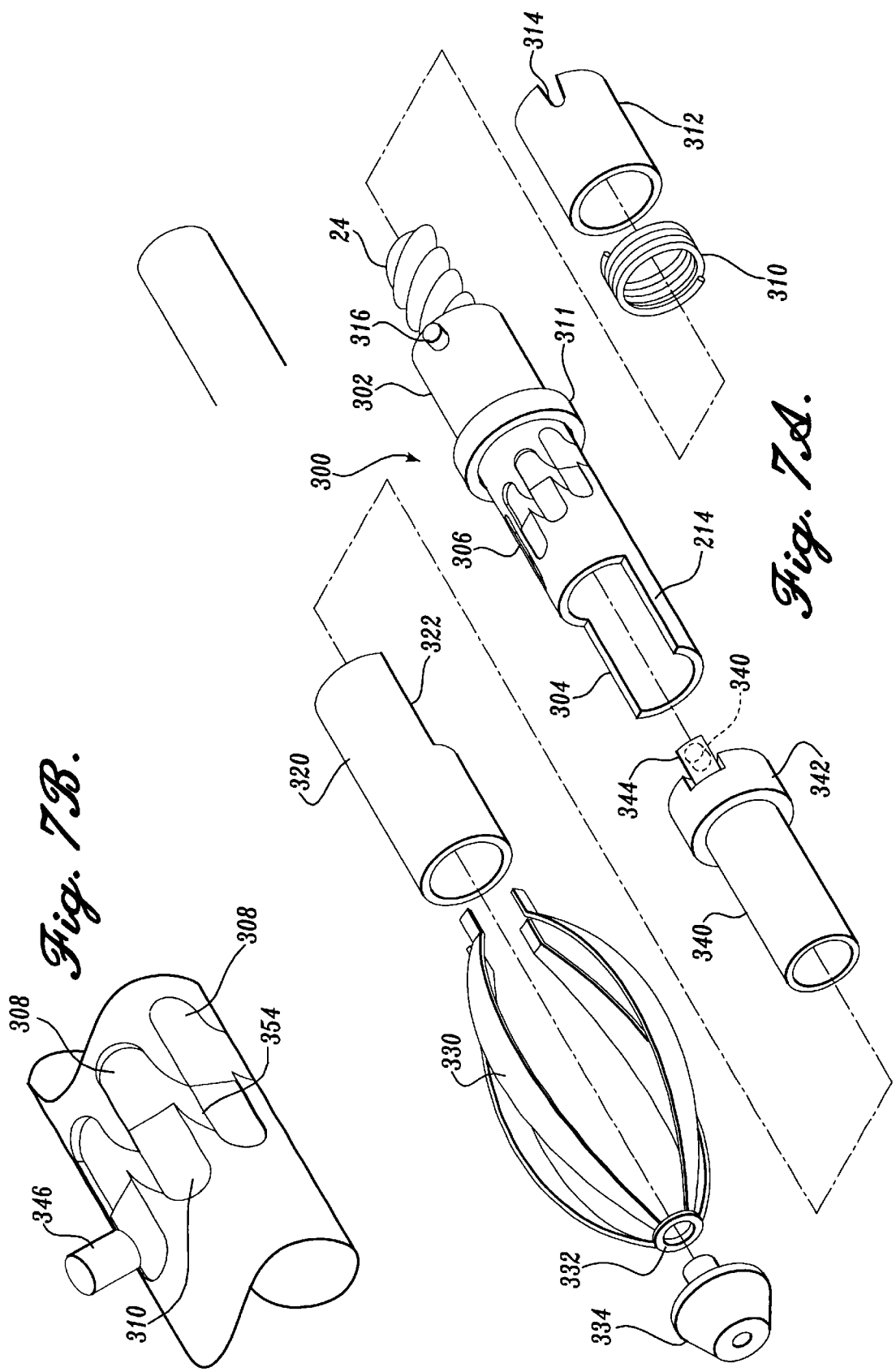

EXPANDABLE ATHERECTOMY BURR

RELATED APPLICATION

This application is a continuation of U.S. patent application Ser. No. 09/178,449, filed Oct. 23, 1998, now U.S. Pat. No. 6,096,054 which in turn claims the benefit of U.S. Provisional patent application No. 60/076,963, filed Mar. 5, 1998, the benefits of the filing dates being claimed under 35 U.S.C. § 120.

FIELD OF THE INVENTION

The present invention relates to medical devices in general, and in particular to atherectomy devices for removing occluding material from a patient's blood vessels.

BACKGROUND OF THE INVENTION

Arteriosclerosis is a common vascular disease in which a patient's blood vessels become hardened and blocked by plaque or clots that impede blood flow. Left untreated, this condition is a major contributing factor to the occurrence of high blood pressure, strokes and cardiac arrest.

To treat arteriosclerosis, many invasive and non-invasive techniques have been developed. For example, cardiac bypass surgery is now a commonly performed procedure whereby an occluded cardiac artery is bypassed with a segment of a healthy blood vessel that is obtained from elsewhere in the body. While this procedure is generally successful, it is fairly traumatic because the entire chest cavity must be opened to access the occluded vessel. Therefore, the procedure is not generally performed on elderly or relatively frail patients.

One example of a promising minimally invasive technique that can be performed on a greater number of patients is to remove the occluding material from a patient's vessel in an atherectomy procedure. To perform this procedure, a guide catheter is typically inserted into the patient's femoral artery and advanced until the distal end of the guide catheter is located in the patient's ostium. A guide wire is then inserted through the guide catheter and traversed into the coronary arteries and past the occluded material to be treated. Then, as described in U.S. Pat. No. 4,990,134, issued to Auth, an atherectomy catheter having a small abrasive burr is advanced through the guide catheter and over the guide wire to the point of the occlusion. The burr is then rotated at high speed and passed through the occlusion to remove particles that are sufficiently small such that they will not reembolize in the distal vasculature. As the burr removes the occlusion, a larger lumen is created in the vessel and blood flow is restored.

It is well recognized that the risk of certain patient complications increases with the size of the guide catheter through which minimally invasive devices are routed. Larger guide catheters require larger access holes in the femoral artery, creating the potential for patient complications, such as the sealing of the puncture site after completion of the procedure. Therefore, physicians generally wish to utilize the smallest possible guide catheter during a procedure. However, the smaller size guide catheters can only accommodate corresponding smaller size ablation burrs. Therefore, if a large vessel is to be treated, a larger burr and corresponding larger guide catheter must be used to successfully remove all of the occlusion from the patient's vessel.

In addition, it has also been discovered that when performing an atherectomy procedure as described earlier, it has been beneficial to remove only a small amount of the occlusion at a time. Therefore, currently many procedures are performed using multiple passes through the occlusion with different sized ablation burrs. While these procedures have proven effective, the use of multiple devices for a single procedure adds both time and cost to the procedure.

Given the disadvantages of the existing atherectomy devices, there is a need for an atherectomy device that can treat different size vessels while being traversed through a small guide catheter.

SUMMARY OF THE INVENTION

To eliminate the need for a physician to utilize larger guide catheters in order to route a larger diameter ablation burr in a patient, the present invention comprises an expandable ablation burr. The ablated diameter preferably has a diameter that exceeds the diameter of a guide catheter through which the burr is routed.

According to one embodiment of the invention, the ablation burr includes a polymeric balloon that expands as the burr is rotated. A portion of the balloon is coated with an abrasive such that the balloon will ablate an occlusion as the burr is rotated and advanced through a vessel.

In another embodiment of the invention, the expandable burr comprises a generally solid core with a nose section having a fixed, maximum outer diameter and a stepped proximal section with a smaller outer diameter. Positioned over the stepped section is a polymeric tube that is coated with an abrasive material. As the burr is rotated, the elastomeric tube expands by centrifugal force, thereby increasing the maximum outer diameter of the burr in order to create a larger lumen in a patient's vessel.

In yet another embodiment of the invention, the ablation burr comprises a mandrel that is secured to a drive shaft. A metallic strip surrounds the mandrel. At least a portion of the metallic strip and mandrel is covered with an abrasive. When the metallic strip is tightly coiled around the mandrel, its outer diameter decreases. When released, the metallic strip will expand to the original outer diameter of the burr.

In yet another embodiment of the invention, the ablation burr includes a wire spring that is wound over a drive tube. A portion of the wire spring is coated with an abrasive material to ablate an occlusion in a patient's vessel as the burr is rotated. A distal end of the spring is coupled to a nose cone that can move axially within the distal end of the drive tube. As the burr is rotated, the nose cone is drawn into the lumen. The maximum outer diameter of the burr is limited by the distance that the nose cone can move within the drive tube.

According to another aspect of the present invention, an ablation burr includes an indexing mechanism which allows the outer diameter of the burr to be selectively adjusted to create varying sized lumens in the patient's vessel. By selectively controlling the length of the burr, the compression of a series of cutting blades that are coupled to the distal and proximal ends of the burr is changed in order to vary the outer diameter of the burr.

In one embodiment, the indexing mechanism includes a tube having a drive tube slidably secured to the proximal end thereof. The drive tube includes a fixed washer disposed at its distal end. The washer includes a number of teeth positioned around a distal rim. Disposed at the distal end of the tube is an indexing ring having a series of slots that encircle the indexing ring. Each slot has a different depth. A slide washer having a set of teeth that engage the teeth on the fixed washer is positioned over the indexing ring and tube.

The slide washer includes a pin that engages a canted edge of the slots as the burr is rotated. The maximum distance that the drive tube can move with respect to a distal end of the burr is limited by the depth of the slot in which the pin on the slide washer is located. By controlling the movement of the drive tube with respect to the distal end of the burr, the maximum outer diameter of the cutting blades is controlled. As the blades are compressed by retrieving the burr into a catheter, the pin on the slide washer is moved to the next slot on the indexing ring such that the outer diameter of the burr can be varied.

In another embodiment of the invention, the indexing mechanism includes a drive tube having a race that extends around the perimeter of the drive tube along an axis that is canted with respect to its longitudinal axis. A traveling ball fits within the race. The drive tube also includes a series of ratchet teeth that extend around the perimeter of drive tube. Positioned over the drive tube is a proximal locking tube having a hole through which the traveling ball extends. Slidably aligned with the proximal locking tube is a distal locking tube that is coupled to the distal end of the ablation burr. Positioned over the proximal and distal locking tubes is a traveling tube having a hole in which a portion of the traveling ball is seated. As the drive tube is rotated with respect to the cutting blades, the traveling ball moves in the race thereby moving the traveling tube along the length of the drive tube and limiting the distance by which the distal end of the burr can move with respect to the proximal end of the burr and hence changing the maximum outer diameter of the cutting blades.

In yet another embodiment of the invention, the indexing mechanism includes a drive tube having a serpentine channel disposed around the perimeter of the drive tube. A proximal locking tube is slidably affixed over the proximal end of the drive tube. A distal locking tube is slidably aligned with the drive tube. The distal locking tube engages a distal end of the ablation burr. Positioned over the drive tube is a traveling tube having a pin that operates as a cam within the serpentine channel. As the pin moves within the channel, the traveling tube limits the movement of the distal locking tube with respect to the drive tube and hence limits the maximum outer diameter of the cutting blades.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 1A and 1B illustrate an expandable balloon ablation burr according to a first embodiment of the present invention;

FIGS. 2A–2D illustrate an ablation burr with an expandable end according to a second embodiment of the present invention;

FIGS. 3A–3D illustrate an expandable burr that is formed from a strip of superelastic material according to a third embodiment of the present invention;

FIGS. 4A and 4B illustrate an expandable spring ablation burr including an indexing mechanism to control the outer diameter of the burr according to another aspect of the present invention;

FIG. 5A illustrates an isometric view of an ablation burr including an indexing mechanism for selectively changing the outer diameter of the burr according to another aspect of the present invention;

FIG. 5B illustrates the ablation burr shown in FIG. 5A with the parts shown in an exploded relationship;

FIGS. 6A and 6B illustrate another embodiment of an ablation burr with an indexing mechanism for selectively changing the outer diameter of the burr according to the present invention; and FIGS. 7A and 7B illustrate yet another embodiment of an ablation burr with an indexing mechanism for selectively changing the outer diameter of the burr according to the present invention.

DETAILED DESCRIPTION OF THE PREFERRED EMBODIMENT

As will be explained in further detail below, the present invention is an ablation burr having an outer diameter that may be expanded to exceed the diameter of a guide catheter through which the burr is routed. Additionally, the present invention is an ablation burr including a mechanism for selectively changing the outer diameter of the ablation burr so that varying sized lumens can be created in a patient's vessel using the same burr.

FIG. 1A illustrates an atherectomy device in accordance with a first aspect of the present invention. The atherectomy device 20 is routed from a position outside a patient's body to a point near the site of a vascular occlusion through a guide catheter 22. Extending through the guide catheter 22 is a drive shaft 24 that is coupled at its proximal end to a source of rotational motion such as an electric motor or gas turbine (not shown) that rotates the drive shaft 24 at high speed, e.g., between 20,000 and 250,000 rpm. Disposed at a distal end of the drive shaft 24 is an ablation burr 28 that when rotated by the drive shaft 24 ablates a new lumen through the occlusion in order to permit blood to flow freely through the vessel. Extending through the drive shaft 24 and the ablation burr 28 is a guide wire 26 that can be steered by a physician in order to guide the ablation burr through the vascular occlusion.

As indicated above, it is generally desirable that the ablation burr 28 be routed through the smallest possible guide catheter to the point near the vascular occlusion. In the past, if the diameter of the vessel in which the occlusion was located was greater than the diameter of the ablation burr, the entire atherectomy device including drive shaft, ablation burr and catheter had to be removed from the patient and replaced with a larger diameter catheter that could accommodate a larger diameter burr if all of the occlusion was to be removed. To facilitate maximal lumen size after ablation, the maximum outer diameter of the ablation burr 28 is expandable such that its maximum diameter exceeds the diameter of the guide catheter used to route the burr to the site of the occlusion.

According to the embodiment of the invention as shown in FIGS. 1A and 1B, the ablation burr 28 comprises a length of hypotube 30 coupled to a distal end of the drive shaft 24. The hypotube 30 includes one or more holes 32 that allow fluid to flow in or out of the hypotube. Surrounding the hypotube 30 is a polymeric balloon 34, having an abrasive 36 disposed on at least a portion of the outer surface of the balloon. The distal end of the ablation burr 28 fits behind a concave surface of a tip 37 that prevents the seal of the polymeric balloon from becoming unglued from the hypotube 30 as the burr is advanced through an occlusion.

When the drive shaft is not being rotated, the balloon 34 collapses into an unexpanded state as shown in FIG. 1A. In its unexpanded state, the outer diameter of the ablation burr 28 is smaller than the inner diameter of the guide catheter 22.

When the drive shaft 24 is rotated, fluid surrounding the drive shaft or within the drive shaft is expelled through the holes 32 in the hypotube causing the balloon 34 to expand to its maximum diameter. The maximum diameter is generally larger than the inner diameter of the guide catheter 22. The burr is then advanced over the occlusion to create a lumen in the patient's vessel. When the drive shaft 24 ceases to rotate, the balloon 34 collapses, and the burr can be removed through the guide catheter 22.

In the presently preferred embodiment of the invention, the polymeric balloon 34 is made from a non-stretchable plastic material such as an oriented polyethylene terephthalate polymer (PET). However, it is believed that other plastics or elastomeric materials may also be used.

The abrasive 36 disposed on the outer surface of the balloon preferably comprises small diamond chips approximately 2–25 microns in size.

If the balloon 34 is made of PET, the abrasive 36 is secured to the balloon by creating a thin base layer of silver using vacuum deposition techniques. Once the base layer is applied to the balloon, a layer of metal such as nickel having a slurry of diamond particles disposed therein can be plated to the base layer using an electro- or electroless plating method as is done with conventional burrs.

In some instances, it may be desirable to etch or mask a portion of the balloon with a pattern of dots or other shapes so that the base layer does not completely surround the balloon. If the abrasive is only plated to the etched pattern, it may allow the balloon to more easily expand and collapse.

In addition to electroplating, it is believed that other techniques could be used to secure the abrasive to the balloon, such as by using an adhesive or chemically bonding sites on the outer surface of the polymeric balloon to which metal ions such as copper, silver, gold, or nickel may bond. These sites may be bonded to the balloon surface using a high-vacuum plasma system or by incorporating chemicals (such as carbon, silver, etc.) with the polymer prior to the extrusion of the balloon. Alternatively, it is believed that pulse cathode arc ion deposition could be used to incorporate bonding sites on the surface of the elastomer.

FIGS. 2A and 2B illustrate another embodiment of an expandable ablation burr according to the present invention. The expandable ablation burr 40 is mounted to the distal end of a conventional drive shaft 24 that rotates the burr at high speeds. A guide wire 26 extends through the drive shaft 24 and the ablation burr 40 so that the burr can guide through a vascular occlusion. The burr is formed as a solid core (except for the lumen through which the guide wire extends) that is made of metal or other suitable material and includes a generally bullet-shaped nose section 42 having a maximum diameter that begins at approximately the midpoint of the burr and tapers in diameter to the distal tip of the burr. The burr 40 also contains a proximal stepped section 44 having a substantially constant diameter that is less than the maximum diameter of the nose section.

Secured over the stepped section 44 of the burr with an adhesive or a mechanical fastener is a polymeric tube 46 having an outer diameter that is substantially equal to or greater than the maximum outer diameter of the nose section 42. The length of the polymeric tube 46 is preferably longer than the length of the stepped section 44 such that a portion of the polymeric tube overhangs the proximal end of the solid core. An abrasive coating is disposed on at least a portion of the outer surface of the tube 46 and the nose section 42. The abrasive is secured to the tube 46 in the same manner as the abrasive is secured to the expandable balloon described above.

When the drive shaft 24 is not rotated, the ablation burr 40 has a maximum outer diameter that is smaller than the inner diameter of a guide catheter 22 through which the burr is routed.

As shown in FIG. 2B, when the drive shaft 24 is rotated, the proximal end of the elastomeric tube 46 expands due to centrifugal force. The proximal end of the ablation burr 40 extends radially outward, therefore allowing the burr to ablate a larger lumen as it is advanced in a vessel. As the drive shaft 24 is slowed, the centrifugal force on the proximal end of the polymeric tube 46 decreases and the outer diameter of the ablation burr returns to its unexpanded state. The ablation burr can then be withdrawn from the patient through the guide catheter 22.

FIGS. 2C and 2D illustrate a cross-section of an alternative embodiment of the expandable ablation burr shown in FIGS. 2A and 2B. An ablation burr 40' includes a generally solid core including a distal nose section 42 and a proximal stepped section 44. A polymeric tube 46' is bonded to the stepped section 44 such that the outer diameter of the polymeric tube is approximately equal to the maximum diameter of the nose section 42 when the burr is in an unexpanded state. In contrast to the embodiment shown in FIGS. 2A and 2B, a proximal end 48 of the polymeric tube 46' is tapered to the drive shaft 24. In addition, the polymeric tube 46' includes one or more holes 50 disposed about its periphery to control the outer diameter of the burr as the burr is rotated.

FIG. 2D illustrates the ablation burr 40' as the drive shaft 24 is rotated. Centrifugal force causes a center section of the polymeric tube that lies between the proximal end of the solid core and the proximal end 48 of the tube to expand radially outward. As the burr begins spinning, centrifugal force expands the polymeric tube. Fluid then fills the interior cavity of the tube and is also acted on by the centrifugal force. To prevent the tube from over expanding, fluid is allowed to vent out the one or more holes 50 that surround the tube 46' such that the volumetric rate at which the fluid vents from the tube reaches an equilibrium with the volumetric rate at which it enters the interior of the tube and the expansion of the tube is halted. The one or more holes 50 increase in size as the speed of the burr increases and the tube expands. As the rotational speed of the ablation burr is decreased, the outer diameter of the burr decreases so that the burr can be withdrawn through the catheter. Because the end 48 of the polymeric tube 46' is closed to meet the drive shaft 24, the polymeric tube 46' is less likely to catch the distal end of the guide catheter as the burr is withdrawn from the patient.

Although the polymeric tube is preferably positioned at the proximal end of the burr, it may be advantageous to place the tube at the distal end of the burr in order to remove certain occlusions.

In simulated ablation tests, the ablation burrs illustrated in FIGS. 2A–2D appear to cause less trauma to the vessel walls and a more even cutting than a conventional burr. In addition, the spinning polymeric tube appears to self center the burr in the center of the patient's vessel. Finally, it is believed that the increased surface area of the polymeric tube creates less heat at the point where it contacts the occlusion, thereby reducing the likelihood of vessel spasm or clotting.

It is currently believed that polymer used to make the polymeric tube should have a stress/strain characteristic that allows the materials to be stretched to a known point but not beyond. One technique to achieve the desired stress/strain characteristics is to stretch the polymeric material as it cools. Alternatively, it is possible to incorporate an inelastic string or band into the tube that straightens as the tube expands and reaches a maximum size but cannot be stretched any further.

In some instances, it may be desirable to coat the outer surface of the core and polymeric tube with a hydrophilic coating such as Hydropass™, available from Boston Scientific and described in U.S. Pat. No. 5,702,754. The hydrophilic coating attracts water molecules, thereby making the surface slippery and easier to advance along the guide catheter. In addition, the hydrophilic coating may be beneficial during ablation since less torque may be transferred to a vessel wall if the burr stalls. In addition, the differential cutting ability of the burr may be enhanced due to the increased ability of the burr to slide over soft tissues.

FIGS. 3A–3D illustrate yet another embodiment of an expandable ablation burr according to the present invention. Secured to the distal end of a drive shaft 24 is a mandrel 60. The mandrel is cylindrical and has a generally bullet-shaped nose at the distal and proximal ends and a central lumen 62 extending through it so that the mandrel may be threaded over a guide wire 26. A central portion 61 of the mandrel has a reduced diameter compared to the maximum diameter of the distal and proximal ends. Surrounding the central cylindrical portion 61 of the mandrel 60 is a metallic strip 64 that is coiled around the mandrel as a spring. The metallic strip 64 preferably has a length that is equal to the length between the bullet-shaped ends of the mandrel 60 and a width that is selected such that the strip wraps completely around the mandrel with some overlap onto itself. The metallic strip 64 includes a tab 66 that is fixed within a corresponding slot 68 disposed on the outer surface of the mandrel as shown in the cross-section FIG. 3B viewed from the distal end of the ablation burr. The tab is secured in the slot with either an adhesive or by welding the tab in the slot.

At least a portion of the outer surface of the metallic strip 64 and the distal end of the mandrel 60 is covered with an abrasive 72 that is plated onto the strip and mandrel in order to ablate a vascular occlusion when the ablation burr is rotated.

FIGS. 3C and 3D illustrate a cross section of the drive shaft, metallic strip, and mandrel. In order to fit the ablation burr within the guide catheter 22, the metallic strip 64 is more tightly wrapped around the mandrel in order to reduce its outer diameter as shown in FIG. 3D. Upon emerging from the distal end of the catheter 22, the metallic strip will spring open to resume its original shape shown in FIG. 3C and its outer diameter will therefore increase. Because the proximal and distal ends of the metallic strip 64 are tapered to follow the contour of the bullet-shaped ends of the mandrel, the metallic strip can be recompressed by pulling it into the distal end of the guide catheter 22.

In the presently preferred embodiment of the invention, the metallic strip 64 is made of a superelastic metal such as Nitinol.

As will be appreciated, to ablate an occlusion in a blood vessel, the metallic strip 64 must be rotated in the direction of the arrow 74 (FIG. 3B) such that an edge 70 of the strip extending along the length of the burr trails the movement of the burr in order to avoid further uncoiling the strip and possibly cutting into the vessel wall.

Yet another alternative embodiment of the expandable ablation burr of the present invention is shown in FIGS. 4A and 4B. The ablation burr 80 includes a coiled wire spring 82 that is wound around the longitudinal axis of a central drive tube 84. Plated to the outer surfaces of at least some of the individual spring coils is an abrasive to ablate an occlusion in a patient's vessel as the burr is rotated. The spring 82 is wound into a generally ellipsoidal shape with a maximum diameter at a midpoint that is larger than the diameter of the guide catheter 22 through which the burr is routed. The distal end of the spring 82 is secured to a nose cone 86 at the distal end of the burr while the proximal end of the spring is secured to the proximal end of the drive tube 84 by a band 85 that overlaps a few proximal coils of the spring.

The drive tube 84 has a proximal lumen 90 into which the distal end of the drive shaft 24 is inserted and secured. A distal lumen 92 of the tube receives a correspondingly shaped shaft 94 that extends from a rear surface of the nose cone 86. The distal lumen 92 and the shaft 94 of the nose cone are shaped such that the shaft moves axially within the lumen but cannot be rotated in the lumen. Therefore, any torque induced in the drive tube 84 by the drive shaft 24 will be transmitted to the nose cone 86 and the distal end of the spring 82. Although not shown in FIGS. 4A and 4B, the drive tube 84 and nose cone 86 preferably include a lumen extending therethrough for passage of a guide wire.

When the ablation burr 80 is positioned in the guide catheter 22 as shown in FIG. 4A, the spring 82 is compressed, thereby reducing its outer diameter. When the ablation burr 80 extends out the distal end of the guide catheter 22, as shown in FIG. 4B, the spring 82 expands into its ellipsoidal shape, thereby increasing the maximum outer diameter of the burr. As the spring 82 expands radially outward, the shaft 94 of the nose cone 86 is drawn into the distal lumen 92. Rotation of the burr will further draw the shaft 94 into the distal lumen 92 until the proximal end of the shaft engages the end of the lumen 92. The length of the lumen 92 and the shaft 94 of the nose cone therefore control the maximum diameter of the spring 82. As a burr is withdrawn into the guide catheter 22, the spring 82 is compressed and the shaft 94 will move distally in the lumen 92.

In many instances, it is desirable to have an ablation burr that can assume several fixed outer diameters. For example, when creating an initial lumen in an occluded vessel, it is generally advisable to utilize the smallest diameter burr available. In the past, if the size of the lumen needed to be increased, the entire ablation burr had to be removed from the patient and successively larger burrs used until a lumen of the desired size was created. To eliminate the need for multiple ablation burrs, another aspect of the invention is an ablation burr with an indexable outer diameter. As the burr is rotated and passed over an occlusion, the outer diameter of the burr can be selectively increased to remove additional occluding material from the vessel.

FIGS. 5A and 5B illustrate a first embodiment of an ablation burr according to the present invention having an indexable outer diameter. The ablation burr 100 is disposed at the distal end of a drive shaft 24. The burr includes a central lumen so that the ablation burr can be passed over a guide wire 104. Surrounding the drive shaft 24 is a catheter 106 having a flared distal end 108 that operates to aid in selectively changing the outer diameter of the burr in a manner described below.

To remove the occluding material from a vessel, the ablation burr includes a number of leaf blades 110 that are secured between a nose cone 112 and a ring 113 at the distal end of the burr. The blades 110 extend proximally over the burr to a leaf retaining ring 114 at the proximal end of the burr. At least a portion of each blade 110 is covered with an abrasive 116 such that when the ablation burr 100 is rotated by the drive shaft 24, the abrasive 116 will remove occluding material from a patient's blood vessel. A polymeric sleeve (not shown) preferably is positioned inside the blades 110 to prevent the blades from causing excessive turbulence in the blood as the burr is rotated.

By selectively changing the distance between the proximal and distal ends of the burr, the amount by which the blades may expand radially outward changes, thereby allowing the burr to create varying sized lumens in a vessel.

As shown in FIG. 5B, to control the diameter of the burr, the ablation burr 100 includes a tube 120 that transmits power from the drive shaft 24 to the distal end of the burr. At the distal end of the tube 120 is an indexing ring 122 having a diameter that is larger than the diameter of the tube 120. In the proximal rim of the indexing ring 122 are a number of slots 124. Each slot includes a first edge 126 that is canted with respect to the longitudinal axis of the tube 120 and a second edge 128 that extends parallel to the longitudinal axis of the tube 120. Each of the slots 124 disposed around the perimeter of the indexing ring has a different depth that controls the outer diameter of the ablation burr.

Pinned to the proximal end of the tube 120 is a drive tube 130. The drive shaft 24 is secured to the proximal end of the drive tube 130. In addition, the drive tube 130 has a central bore through which the tube 120 can fit. The drive tube 130 includes a longitudinally extending slot 132 on its outer surface into which a pin 134 is fitted. The pin 134 is secured to the outer surface of the tube 120 so that the tube 120 can move longitudinally within the drive tube 130 but torque from the drive tube 130 is transferred to the tube 120 or vice versa.

At the distal end of the drive tube 130 is a fixed washer 136. The fixed washer 136 has a diameter that is larger than the diameter of the drive tube 130. The distal rim of the fixed washer 136 includes a number of teeth 138.

Positioned over the indexing ring 122 is a slide washer 140. The slide washer 140 has an inner diameter substantially equal to the outer diameter of the indexing ring 122 and an outer diameter substantially equal to the outer diameter of the fixed washer 136. The proximal rim of the slide washer 140 contains a number of teeth 142 that mate with the teeth 138 of the fixed washer 136. The slide washer 140 also includes a pin 144 that rides along the edges 126 and 128 of the slots 124 in the indexing ring 122. Finally, the burr includes a spring 150 disposed between the back surface of the ring 113 and the distal end of the slide washer 140.

When rotated by the drive shaft 24, centrifugal force causes the blades 110 to be radially expanded, thereby compressing the tube 120 and the drive tube 130. This in turn causes the pin 144 to slide along a canted edge 126 of a slot 124 in the indexing ring 122. As the pin 144 travels along the canted edge 126, the teeth 142 on the slide washer 140 rotate with respect to the teeth 138 on the fixed washer 136. The maximum distance by which the drive tube 130 can be compressed over the tube 120 is limited by the depth of the slots 124 extending around the index ring 122, thereby limiting the diameter of the burr.

To index the ablation burr to its next outer diameter, the burr is pulled into the catheter 106. The flared distal end 108 of the catheter engages the blades 110 and compresses them and the spring 150 causes the pin 144 on the slide washer 140 to travel along the straight edge 128 of a slot 124 to a position proximal to the slots of the indexing ring 122. The force of the spring 150 pushes the slide washer 140 proximally thereby causing the teeth 142 on the slide washer and the teeth 138 on the fixed washer to seat and further rotate the pin 144 to the next slot around the indexing ring 122.

In operation, a physician sets the diameter of the burr to the smallest setting to ablate an initial lumen in the patient's vessel. Then, by sequentially spinning the burr, stopping it and retracting it into the catheter, the diameter can be increased or decreased depending on the position of the pin 144 over the indexing ring 122 until a desired lumen diameter is reached.

In the presently preferred embodiment of the invention, the various components of the indexable burr 100 are made by micro-machining. However, it is believed that other fabrication techniques such as metal injection molding could also be used.

FIGS. 6A and 6B illustrate another embodiment of an indexable ablation burr according to the present invention. The ablation burr 200 includes a drive tube 204 into which the distal end of the drive shaft 24 is inserted and secured. The drive tube 204 also includes a race 206 that circumscribes the perimeter of the drive tube. The race 206 is canted with respect to the longitudinal axis of the drive tube such that the race traverses a portion of the length of the drive tube 204. A traveling ball 208 rests within the race 206.

Disposed distal to the race 208 is a series of ratchet teeth 210 that are cut into the outer surface of the drive tube 204. The teeth operate to discretely step the maximum outer diameter of the ablation burr and to transfer the rotational motion of the drive shaft 24 to the burr in conjunction with a rachet tab 216 as described below.

Disposed over the proximal end of the drive tube 204 is a proximal locking tube 212. The proximal locking tube 212 is generally cylindrical but has a stepped section 214 at its distal end such that half the perimeter of the proximal locking tube 212 is removed. The locking tube 212 also includes a ratchet tab 216 that extends inwardly from the inner surface of the locking tube in approximately the middle of the stepped section 214. The ratchet tab 216 engages the ratchet teeth 210 when the proximal locking tube 212 is positioned over the drive tube 204. Finally, the proximal locking tube 212 includes a hole 218 that is cut in the outer surface of the locking tube 212 at a position proximal to the stepped section 214. The hole 218 is sized such that a portion of the traveling ball 208 will extend through the hole 218 when the proximal locking tube 212 is positioned over the drive tube 204.

Axially aligned with the distal end of the drive tube 204 is a distal locking tube 220. The locking tube 220 is generally cylindrical but has a stepped section 222 at its proximal end that mates with the stepped section 214 of the proximal locking tube 212 when the proximal and distal locking tubes are axially aligned. The stepped sections 214 and 222 maintain a rotational coupling between the distal and proximal ends of the ablation burr while allowing the distance between the proximal and distal locking tubes to vary.

Surrounding the burr are a number of blades 226 that extend radially outward from a ring 228. The ring 228 is held in place between a nose cone 230 and a locking ring 232 at the distal end of the burr. The locking ring is secured to the distal end of the distal locking tube 220. The blades 226 are folded back over the outside of the burr and are secured around the proximal end of the locking tube 212 by a leaf retaining ring 236. Although not shown, the ablation burr 200 preferably includes a polymeric liner inside the blades 226 to prevent the blades from causing excessive turbulence in the patient's blood as the burr is rotated.

Finally, the ablation burr 200 includes a traveling tube 240 that fits over the proximal and distal locking tubes 212 and 220. The traveling tube 240 includes a hole 242 disposed in its perimeter. The hole forms a detent into which a top portion of the traveling ball 208 is seated. The distal rim of the traveling tube 240 engages the rear or the. proximal surface of the ring 228 from which the blades 226 extend.

To expand or contract the ablation burr 200, the drive shaft 24 is rotated in a direction that is opposite to the direction used during ablation while the blades 226 are held stationary. The ablation burr 200 is retracted into a catheter having a distal end that captures the blades and holds them still as the drive shaft is rotated.

As shown in FIG. 6B, when the drive tube 204 is rotated in the clockwise direction, the ratchet tab 216 rides over the ratchet teeth 210. This causes the traveling ball 208 to move in the race 206 that extends around the outer surface of the drive tube 204 thereby pushing the traveling tube 240 proximally or distally with respect to the drive tube 204. Because the distal rim of the traveling tube 204 engages the rear or proximal surface of the ring 228 from which the blades 226 extend, the distance between the proximal and distal ends of the blades is varied and hence the maximum expansion of the ablation burr is controlled.

When the drive tube 204 is rotated in the counterclockwise direction and the blades 226 are free, the ratchet teeth 210 engage the ratchet tab 216 causing the traveling tube to rotate with the burr and leaving the traveling ball 208 in the same place in the race 206. Centrifugal force on the blades 226 will cause the nose cone 230 to be drawn proximally until the rear surface of the ring 228 engages the distal rim of the traveling tube 240 and the expansion of the burr is halted. Therefore, by changing the position of the traveling tube 240 over the main tube 204, the maximum diameter of the burr is controlled.

In operation, the physician may position the traveling ball in the race such that the burr has a minimum diameter in order to create an initial lumen in a vessel. Then the burr is then withdrawn into the catheter to hold the blades and the position of the traveling ball changed to increase the size of the lumen without having to remove the atherectomy device from the patient.

Again, parts of the ablation burr 200 are preferably made by machining but could be made by other techniques such as metal injection molding.

FIGS. 7A and 7B show another alternative embodiment of an indexable ablation burr according to the present invention. The ablation burr 300 includes a drive tube 302 into which the distal end of the drive shaft 24 is inserted and secured. The drive tube 302 is generally cylindrical except for a stepped semi-circular section 304 at the distal end of the tube, whereby half the circumference of the tube is removed. The drive tube 302 also includes a serpentine channel 306 disposed about the outer surface of the tube proximal to the stepped section 304. The serpentine channel 306 operates to control the maximum diameter of the ablation burr in a manner described below.

Disposed over a proximal end of the drive tube 302 is a spring 310. The spring abuts a ring 311 that is formed around the perimeter of the drive tube 302 to prevent the spring from moving forward on the drive tube. Also disposed over the proximal end of the drive tube 302 behind the spring 310 is a proximal locking tube 312. At its proximal rim, the proximal locking tube 312 includes a notch 314 into which a pin 316 that extends radially outward from the proximal end of the drive tube 302 is inserted. The pin 316 operates to transfer rotation energy of the drive tube 302 to the proximal locking tube 312 while allowing the locking tube 312 some axial motion along the drive tube.

Positioned distal to and axially aligned with the drive tube 302 is a distal locking tube 320. The distal locking tube 320 is generally circular with a stepped semi-circular section 322 that mates with the stepped section 304 on the drive tube 302. At the distal end of the burr are a set of blades 330 that extend outwardly from a ring 332 and are held in place at the distal end of the burr by a nose cone 334 and a retaining ring (not shown). The retaining ring is secured within the distal end of the distal locking tube 320. As with the indexable burrs described above, an elastomeric liner is preferably positioned inside the blade to prevent excessive turbulence of the blood in a lumen.

Extending over the drive tube 302 and the distal locking tube 320 is a traveling tube 340. At its proximal end, the traveling tube 340 includes a larger diameter flange 342 with a proximally extending tab 344 secured thereto. Extending radially inward from the end of the tab 344 is a follower pin 346.

As shown in FIG. 7B, the tab 344 and follower pin 346 operate as a cam within the serpentine track 306 that is formed around the outer surface of the drive tube 302. The track 306 includes a number of alternating bends 308, 310 that open towards the distal and proximal ends of the drive tube 302, respectively. Each of the bends 308 that open towards the distal end of the drive tube 302 are located at a different position along the length of the drive tube 302.

The depth of the channel 306 varies as the channel proceeds around the drivetube 302. Positioned in the channel near each of the bends 308, 310 is a step 354. At each step, the depth of the channel increases. The depth then decreases in the channel until the next bend where the depth again increases with a step. This pattern continues around the circumference of the drive tube 302.

As the ablation burr 300 is pulled into a catheter having a distal end which prevents the collapse or bending of the blades 330, a pull on the drive coil causes retraction of the drive tube 302. This causes a relative movement of the traveling tube 340 in a distal direction (relative to the drive tube). The follower pin 346 will move to a distal end of the slot in the serpentine channel 306. Releasing the drive coil will allow spring 310 to move the drive tube 302 distal which will result in the traveling tube pin moving into a proximal end of the slot in the serpentine channel 306. As the pin 346 moves back and forth in the channel, it is forced to move in one direction due to a series of ramps in the channel. As the pin 346 moves to the distal end of a slot, it moves over a ramp which prevents it from returning back down that slot. It is forced to return at an angle down to the adjacent slot. Before reaching the bottom of the adjacent slot, it again travels over a ramp, which prevents it from returning up the slot it had just traveled down. The pin is now in an analogous position to the position in which it started. Because the proximal end of each slot is at a slightly different position (along a proximal/distal line on the drive tube), the overall length of the burr is therefore adjusted with each proximal/distal movement of the pin.

As can be seen from the above description, the present invention provides various mechanisms for selectively controlling the diameter of an ablation burr. By controlling the diameter of the burr, it is not necessary to remove the burr, drive shaft and catheter in order to ablate a larger diameter lumen in a patient.

While the preferred embodiments of the invention has been illustrated and described, it will be appreciated that various changes can be made therein without departing from the spirit and scope of the invention. The scope of the invention should therefore be determined from the following claims and equivalents thereto.

The embodiments of the invention in which an exclusive property or privilege is claimed are defined as follows:

1. An atherectomy device for ablating an occlusion in a patient's blood vessel, comprising:

a drive shaft;

a drive tube coupled to the distal end of the drive shaft;

a nose cone that slides within a lumen at a distal end of the drive tube, wherein the nose cone and the lumen at the distal end of the drive tube have a cooperating shape such that they can slide axially with respect to one another but cannot rotate with respect to one another;

a wire spring having a first end coupled to a proximal end of the drive tube and a second end coupled to the nose cone, the wire spring having an outer diameter that increases as the drive shaft is rotated, the outer diameter of the wire spring being limited by a length of travel of the nose cone in the lumen at the distal end of the drive tube; and an abrasive disposed on an outer surface of the wire spring.

* * * * *

UNITED STATES PATENT AND TRADEMARK OFFICE
CERTIFICATE OF CORRECTION

PATENT NO.     : 6,416,526 B1                                                    Page 1 of 1
DATED          : July 9, 2002
INVENTOR(S)    : M. Hefner It is certified that error appears in the above-identified patent and that said Letters Patent is hereby corrected as shown below:

Title page,
Item [12], Inventor, "Wyzgala et al." should read -- Hefner --
Item [75], Inventors, "Inventors: Mark Wyzgala, Bellevue; Donald Baumgarten, Seattle; Lucas S. Gordon, Redmond; Eric B. Hamilton, Bothell; Matt Hefner, Puyallup; Tom Hiblar, Everett; Edward Wulfman, Woodinville, all of WA (US)" should read -- Inventor: Matt Hefner, Puyallup, WA (US) --

Signed and Sealed this

Twenty-eighth Day of October, 2003

JAMES E. ROGAN
*Director of the United States Patent and Trademark Office*